United States Patent
Ma

(10) Patent No.: US 9,687,839 B2
(45) Date of Patent: Jun. 27, 2017

(54) REGENERATION OF CATALYST FOR HYDROGENATION OF SUGARS

(71) Applicant: Archer Daniels Midland Company, Decatur, IL (US)

(72) Inventor: ChiCheng Ma, Forsyth, IL (US)

(73) Assignee: Archer Daniels Midland Co., Decatur, IL (US)

(*) Notice: Subject to any disclaimer, the term of this patent is extended or adjusted under 35 U.S.C. 154(b) by 0 days.

(21) Appl. No.: 15/223,401

(22) Filed: Jul. 29, 2016

(65) Prior Publication Data

US 2016/0332154 A1    Nov. 17, 2016

Related U.S. Application Data

(62) Division of application No. 14/834,677, filed on Aug. 25, 2015, now Pat. No. 9,427,733, which is a division of application No. 14/400,156, filed as application No. PCT/US2013/036901 on Apr. 17, 2013, now Pat. No. 9,144,797.

(60) Provisional application No. 61/651,021, filed on May 24, 2012.

(51) Int. Cl.

| C07C 29/132 | (2006.01) |
| B01J 38/48 | (2006.01) |
| B01J 23/94 | (2006.01) |
| C10G 3/00 | (2006.01) |
| B01J 38/54 | (2006.01) |
| B01J 21/18 | (2006.01) |
| B01J 23/46 | (2006.01) |
| B01J 23/96 | (2006.01) |
| B01J 25/02 | (2006.01) |
| B01J 25/04 | (2006.01) |
| B01J 23/755 | (2006.01) |
| B01J 38/64 | (2006.01) |
| C07C 29/141 | (2006.01) |
| B01J 38/06 | (2006.01) |
| B01J 38/70 | (2006.01) |
| B01J 38/60 | (2006.01) |

(52) U.S. Cl.
CPC ............... *B01J 38/48* (2013.01); *B01J 21/18* (2013.01); *B01J 23/462* (2013.01); *B01J 23/755* (2013.01); *B01J 23/94* (2013.01); *B01J 23/96* (2013.01); *B01J 25/02* (2013.01); *B01J 25/04* (2013.01); *B01J 38/06* (2013.01); *B01J 38/54* (2013.01); *B01J 38/60* (2013.01); *B01J 38/64* (2013.01); *B01J 38/70* (2013.01); *C07C 29/132* (2013.01); *C07C 29/141* (2013.01); *C10G 3/50* (2013.01); *C10G 3/62* (2013.01); *Y02P 30/20* (2015.11)

(58) Field of Classification Search
CPC ......... C07C 29/132; B01J 38/48; B01J 23/96; B01J 25/04
See application file for complete search history.

(56) References Cited

U.S. PATENT DOCUMENTS

| 5,495,055 A * | 2/1996 | Rueter ..................... B01J 23/96 568/876 |
| 2011/0009614 A1 * | 1/2011 | Blommel ................. B01J 38/10 536/124 |
| 2011/0196181 A1 * | 8/2011 | Becker ..................... C07C 5/10 585/269 |

\* cited by examiner

*Primary Examiner* — Sudhakar Katakam

(74) *Attorney, Agent, or Firm* — Vincent T. Kung

(57) ABSTRACT

A process for regenerating catalysts that have been deactivated or poisoned during hydrogenation of biomass, sugars and polysaccharides is described, in which polymerized species that have agglomerated to catalyst surfaces can be removed by means of washing the catalyst with hot water at subcritical temperatures. A feature of the process can regenerate the catalysts in situ, which allows the process to be adapted for used in continuous throughput reactor systems. Also described is a continuous hydrogenation process that incorporated the present regeneration process.

10 Claims, 7 Drawing Sheets

REGENERATION OF CATALYST FOR HYDROGENATION OF SUGARS

RELATED APPLICATIONS & BENEFIT OF PRIORITY

The present application is a divisional of U.S. patent application Ser. No. 14/834,677, filed Aug. 25, 2015, which is a divisional of U.S. patent application Ser. No. 14/400,156, filed Nov. 10, 2014, which claims benefit of priority of International Application No. PCT/US13/36901, filed Apr. 17, 2013, which claims priority to U.S. Provisional Application Ser. No. 61/651,021, filed May 24, 2012, the entire contents of each are incorporated herein by reference.

FIELD OF INVENTION

The present invention relates to a process for regenerating catalysts that have been deactivated or poisoned during hydrogenation of biomass or biomass derivatives. In particular, the invention describes a regeneration process that can bring back catalyst activity in hydrogenation reactors of sugars or polysaccharides, and an associated reactor system.

BACKGROUND

In recent years, interest in developing renewable and "green" resources for chemical and fuel products has gained considerable momentum. In this respect, the exploitation of biomass or bio-based materials (i.e., materials whose carbon content is derived from regenerative biological rather than non-regenerative sources) for generating chemical and fuel products, which until now have been predominantly derived from fossil-origin materials, such as petroleum or coal, has become a focus of research and developmental investment. Certain chemical and fuel product replacements or alternatives have been produced on a commercial scale from biomass. For example, in the area of liquid fuels, ethanol and biodiesel (i.e., fatty acid alkyl esters) have been produced on a commodity scale from corn and sugar cane (for ethanol) and from various vegetable oils and animal fats. Even for these examples, though, biomass utilization processes can be improved.

Common raw materials derived from the processing of biomass are carbohydrates or sugars, which can be treated chemically to modify the carbohydrates into other useful chemicals. Thermal treatments provide a method to transform complex biomass, such as forest and agricultural residues into liquid oils. In a hydrothermal liquefaction (HTL) process, conversion of carbohydrates is done with wet biomass at elevated temperatures (e.g., 300°-350° C., 570°-660° F.). Steam generated by heating the wet biomass results in high pressures (e.g. 15-20 MPa, 2,200-3,000 psi). Typically, the conversion is processed in a matter of minutes (e.g., 5-20 minutes).

Another such chemical treatment process is to hydrogenate carbohydrates into polyhydric alcohols, which in turn can themselves be further processes into other useful materials or biofuels. Sugar alcohols, such as xylitol, sorbitol, and lactitol, are industrially most commonly prepared by catalytic hydrogenation of corresponding sugar aldehydes over sponge-metal catalysts, such as nickel and ruthenium on carbon catalysts.

Coking and catalyst deactivation is a problem that arises from the hydrogenation of sugar alcohols because of the presence of residual sugars and high molecular weight polymers that have a degree of polymerization (DP) number greater than 3 in sugar alcohol solutions.

In many cases process designs, costs and operation schedules are greatly affected by the presence of catalyst poisons. Presence of oxidizing agents or small amounts of deactivators can cause either deactivation or poisoning of the hydrogenation catalyst. Sometimes the reaction product, reaction intermediates or by products act as catalytic deactivators and do not allow completion of the primary reaction.

In large scale sugar hydrogenation, catalyst deactivation often plays a central role in the economic efficiency of the hydrogenation process, such as life cycle assessment (LCA). Deactivation of the catalyst can be a complex phenomenon because active sites on catalyst may be blocked by bulky molecules through physical absorption, or poisoned by impurity in the feed stream, or absorbance of reactants, intermediates and products. Among of the latter, catalyst poisoning by impurities, such as sulfur compounds, is a key factor for catalyst deactivation. Although, in general, the amount of sulfur contained in biomass is relatively small, however, at large volumes and over time even minimal amounts can build up and adversely affect catalyst activity. Some biomass can contain as much as 0.5 wt. % sulfur. This poisoning impurity has strong interaction with catalyst surface and can be irreversible.

In a particular situation, one of the problems encountered in the catalytic hydrogenation of aldose sugars is the deactivation and instability of the hydrogenation catalyst, for example due to the formation of harmful by-products, such as epimers, hydrolysis products and their reduction products. Aldonic acids, such as lactobionic acid and xylonic acid, represent one example of the harmful by-products formed in the hydrogenation of aldoses to alditols. In the hydrogenation of glucose, it has been found that gluconic acid is typically formed as a by-product. It has also been found that gluconic acid has a tendency to adhere to the catalyst surface thus occupying the active sites of the hydrogenation catalyst and deactivating the catalyst. The deactivation and instability of the catalyst also lead into problems in the recovery and regeneration of the catalyst. These problems are even more severe especially with recycled catalysts. Recovery of the catalyst by filtration can be difficult.

In view of the foregoing, care should be taken to minimize presence of catalytic deactivators and poisons in the reaction mixture so as to prolong life of the catalyst. Under such situations some may either opt to use a different type of catalyst or seek to clean or regenerate the catalyst.

Regeneration of deactivated catalysts is possible for many catalytic processes and is widely practiced. The main purpose is to remove the temporary poisons on the catalyst surface and restore the free adsorption sites. Generally regeneration processes can be categorized into two types, i.e., off-site and on-site regeneration. In the off-site (ex-situ) regeneration, the catalyst is unloaded from the reactor and regeneration is performed in moving-bed belt calciners or conical-shaped rotating drum calciners. (See, Robinson, D. W., Catalyst Regeneration, Metal Catalysts. *Kirk-Othmer Encyclopedia of Chemical Technology* [online]. 4 Dec. 2000). The on-site (in-situ) regeneration does not require removing the catalyst from a reactor. Commonly, the procedure is to burn off, or oxygenate, the temporary poisons, such as green oil, in order to resume catalyst activity. Regeneration of the catalyst may be accomplished, for example, by heating the catalyst in air to a temperature over 300° C., up to about 500° C., to incinerate any organic material, polymers, or char. Catalyst regeneration using such techniques, however, has certain limits; one is that repeated regeneration operations can cause permanent degradation of the catalyst activity.

Another approach is using hot-compressed water as alternatives to organic solvents and as a medium for unique and/or green chemistry to extract a variety of organic compounds has grown over the recent decade. (Adam G. Carr et al., *A Review of Subcritical Water as a Solvent and Its Utilization for Processing of Hydrophobic Organic Compounds*, CHEMICAL ENGINEERING JOURNAL, v. 172 (2011), pp. 1-17, contents of which are incorporated herein by reference. See also, e.g., M. Osada et al., ENERGY & FUELS 2008, 22, 845-849, contents incorporated herein by reference, pertaining to regenerate catalysts poisoned by sulfur.) Of particular interest are processes in water at or near its critical point ($T_c$=374° C., $P_c$=221 bar (~3205.33 psi), and $p_c$=0.314 g/ml). Although some have explored the use of subcritical water as a solvent and its utility for hydrophobic organic compounds, different kinds of reaction materials and catalytic substrates bring their own associated and distinguishable issues. The reversal of the solvent characteristics of critical hot-compressed water also results in precipitation of salts that are normally soluble in room temperature water. Most inorganic salts become sparingly soluble in supercritical water. This is the basis for unique separation of ionic species in supercritical water. The precipitated salts can serve as heterogeneous catalysts for reactions in supercritical water.

In view of the various problems and limitations current regenerative techniques, a better process for regenerating catalysts used in sugar hydrogenation would be appreciated.

SUMMARY OF THE INVENTION

The present invention describes, in part, a method of reducing catalytic contamination from sugars or sugar alcohol hydrogenation. The method includes: applying a deionized aqueous rinse to a skeletal catalyst or sponge-metal catalyst at a subcritical temperature when catalytic activity of the catalyst decreases to a predetermined level.

Alternatively, the invention describes a method of regenerating hydrogenation catalyst activity in-situ for hydrothermal processing of sugars or polysaccharides. In particular, the method involves: a) providing a hydrogenation reactor, the reactor being configured to have at least a first and a second vessel, the first vessel having a first catalyst and the second vessel having a second catalyst, the first and second catalysts being either the same or of a different material; and b) rinsing each respective vessel and catalyst with subcritical deionized water of between about 130° C.-250° C. for an extended period.

Depending on the catalyst material, the method further involves: introducing a subcritical deionized aqueous solution containing $H_2O_2$ in a concentration of ≤7% by volume to a first catalyst in the first vessel of the reactor when catalytic activity of the first catalyst decreases to a predetermined level; introducing periodically an aqueous salt solution to either 1) the first catalyst in the first vessel or 2) the second catalyst in the second vessel of the reactor (when catalytic activity of the second catalyst decreases to a predetermined level); removing respectively the aqueous $H_2O_2$ solution from the first vessel and aqueous salt solution from the first or second vessels of the reactor; and rinsing each vessel and respective catalyst with subcritical deionized water of between about 130° C.-220° C.

The aqueous $H_2O_2$ solution is applied to the first catalyst in the first vessel once (1) for each one to eight (1-8) applications of aqueous salt solution applied to the second catalyst in the second vessel, or as catalytic performance needs may dictate.

In another aspect, the present invention also pertains to a continuous hydrogenation process, which involves a hydrogenation reactor system with an in-take port and an extraction port, each of which is connected in-line to an in-bound channel and an out-bound channel, respectively. Introduce a carbohydrate or sugar solution feedstock and hydrogen into a reactor having a catalyst therein. React the feedstock under pressure; remove the resulting aqueous reaction product mixture; and periodically introduce a subcritical deionized water rinse into the first reactor when catalytic activity of the catalyst decreases to a predetermined level. In certain embodiments, the reactor system is configured with a first reactor section and second reactor section, each involving a different kind of catalyst material, such that a first part reaction involves a first catalyst material and a second part reaction involves a second catalyst material. The first and second reactor sections are arranged either in serial communication relative to each other. There may be a parallel second reactor section.

Alternatively, each of the first and second reactors has a first reactor chamber and at least a parallel second reactor chamber. The first reactor chamber is used alternatively with the parallel second reactor chamber, such that a reactor chamber is washable with the subcritical deionized water rinse at a given time, without interruption of said hydrogenation process. Additionally, one can introduce a deionized aqueous solution containing $H_2O_2$ in a concentration of 6% or 7% by volume to the first catalyst in the first reactor for a period of up to 18 hours when catalytic activity of that first catalyst decreases to a predetermined level. Alternatively, one can rinse with an aqueous 1% to 10% concentration salt solution at a temperature between 60° C. to 105° C. over a period of 6-22 hrs.

The two washing cycles are separate and distinct from each other, hence they can be performed independently of each other. That is the first wash does not necessarily influence catalyst regeneration in the second reactor chamber.

Additional features and advantages of the present methods will be disclosed in the following detailed description. It is understood that both the foregoing summary and the following detailed description and examples are merely representative of the invention, and are intended to provide an overview for understanding the invention as claimed.

DETAILED DESCRIPTION OF THE INVENTION

Section I—Definition of Terms

Figure 1:
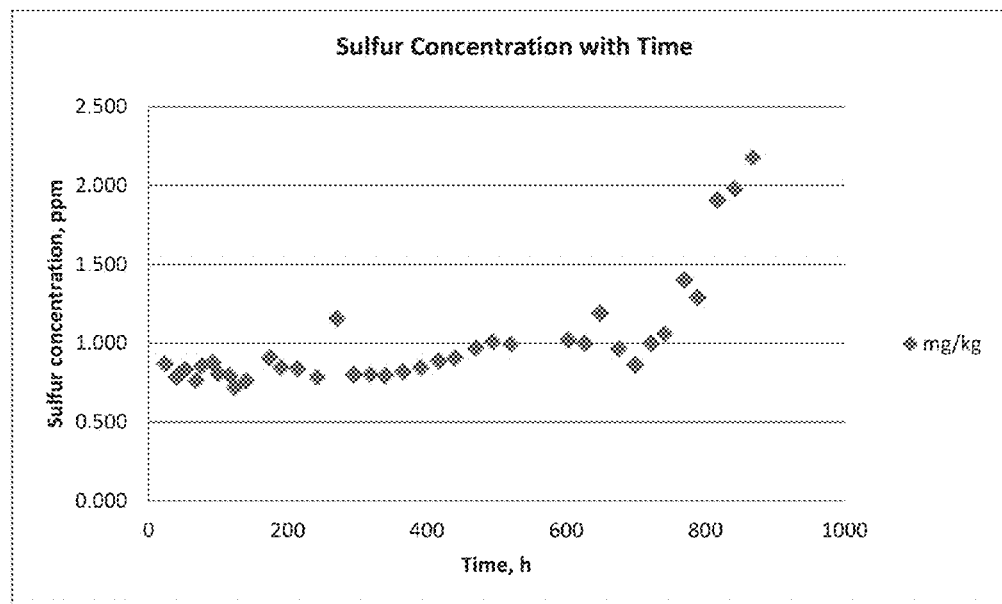
FIG. 1 is a graph showing an increase of sulfur concentration over time in a skeletal catalyst or sponge-metal catalyst, such as a Raney nickel, fixed-bed reactor, which illustrates a problematic condition that leads to catalyst poisoning and deactivation.

Before describing the present invention in detail, certain terms that have meanings generally understood by those of ordinary skill in the art are nevertheless defined herein to better distinguish nuances in meaning that may apply to different embodiments of the invention. It is understood that the definitions provided herein are intended to encompass the ordinary meaning understood in the art without limitation, unless such a meaning would be incompatible with the definitions provided herein, in which case the definitions provided control. The present invention is not necessarily limited to specific compositions, materials, designs or equipment, as such may vary. As used in this specification and the appended claims, the singular forms "a," "an," and "the" include plural referents unless the context clearly dictates otherwise.

The term "carbohydrate" as used in the specification and claims includes monosaccharides and polysaccharides. This term includes both pure compounds, such as glucose and sucrose, and mixtures such as cornstarch hydrolyzate, which is a hydrolysis product of cornstarch containing glucose (dextrose) and oligomers thereof.

The term "polysaccharide" as used in the specification and claims includes those saccharides containing more than one monosaccharide unit. This term encompasses disaccharides and other saccharides containing a small number of monosaccharide units, which are commonly known as oligosaccharides.

The term "catalyst poisoning" as used herein refers to an irreversible adsorption on or reaction with the active surface of a catalyst by reaction product species or impurities (e.g., hydrogen sulfide, cysteine methionine.)

The term "conversion" as used herein refers to hydrogenation when applied to monosaccharides and to a combination of hydrogenation and hydrolysis when applied to polysaccharides.

The term "fouling" as used herein refers to the formation of coke on catalyst surfaces that block the active sites of the catalyst. Sugar alcohols or polymerized species can undergo dehydration or proteins undergo denaturation to form polymers that obstruct catalyst surfaces.

The term "subcritical water" as used herein refers to an intermediate state of water above its boiling point at ambient pressure (>100° C., at 0.1 MPa) and below its critical point (≥374° C., at ≥22.1 MPa). For instance, temperature and pressure windows like 150<T<370° C. at 0.4<p<22 MPa, 300≤T≤350° C. at 10≤p≤18 MPa and 250° C.≤T≤450° C. at $p > p_{critical}$ have been reported. Sometimes other terminology, such as "hot compressed water" (HCW), has been employed generally to refer to water at temperatures above 150° C. and various pressures, or "high-temperature water" (HTW), defined broadly as liquid water above 200° C. The term is used to distinguish processes that are performed below the critical point, but above the boiling point from reactions in supercritical water. Subcritical water has a controlled temperature and pressure in a range less than that of the critical point according to the requirement of application. Subcritical water can be used as an inexpensive, non-toxic, non-flammable, clean solvent in organic chemical research and commercial applications.

Section II—Description

Sponge-metal catalyst are used to convert sugars, such as dextrose, pentose, or glucose to sorbitol and xylose to xylitol, by pressure hydrogenation/hydrogenolysis. A problem that arises frequently is the poisoning of the catalyst and consequent reduction of catalytic function over time. The life of hydrogenation catalysts typically lasts on average between about 70-95 hours (usually about 80-85 hours) before experiencing a significant loss of active functionality. This poisoning often results from agglomeration of oligomers and sulfur compounds to the catalyst surface, which reduces active surface area.

For instance, as in FIG. 1, the concentration of organic or biological-derived sulfur from a feedstock increases with time. Sulfur is absorbed on catalyst surfaces until the absorption capacity reaches maximum. After about 700-800 hours of use, the amount of sulfur that agglomerates to sponge-metal (e.g., Raney nickel) catalysts in a fixed-bed reactor increases steeply. A typical fresh Raney nickel catalyst possesses on average an active surface area of about 42 $m^2$ per gram. After reacting, the active surface area of the catalyst is reduced on average to about 21 $m^2$ per gram, which is almost a 50% reduction. Chemi-absorption analysis shows that the deactivation mechanism appears to involve polymer materials covering the catalytic surface and sulfur compounds binding with the nickel. As more sulfur and oligomers agglomerate on catalyst surface, the overall ability of the catalyst to reduce sugars decreases and the amount of residual sugar increases.

In view of difficulties and issues with some regenerative techniques, an attribute of the present invention is to provide a catalyst regeneration process that can bring back catalyst activity, and thereby increase the efficiency of sugar hydrogenation conversion on the regenerated catalyst. Unlike the issues associated with sulfur compounds that one may encounter when processing hydrocarbons in the petrochemical industry, hydrogenation and hydrogenolysis of biologically-derived sugars and other carbohydrates or oils have presented new and unique challenges. Such reactions are performed at temperatures lower than 250° C., typically less than about 230° C., which is far less than and outside the operational temperature range employed in petrochemical refining.

The present invention presents one solution to these problems. In part, the present invention is directed to the removal or minimization of the agglomeration and build-up of sulfur as well as organic compounds on the catalyst surface with deionized subcritical water as a solvent. The present invention provides a solution that enables industrial users in continuous production processing to regenerate the activity of catalyst substrates in-situ while the reactor remains "online."

A

According to an aspect of the present invention, the method of regenerating hydrogenation catalyst activity in-situ involves providing a either a batch or continuous feed hydrogenation reactor containing a catalyst. The reactor can be configured to have a first and a second vessel, each vessel containing a catalyst. Then rinsing each vessel and catalyst with subcritical deionized water of between about 130° C.-250° C. for an extended period, such as, 3-4 hours.

Subcritical water at temperatures below about 120° C. or 125° C. did not exhibit sufficient effective cleaning ability of catalyst surfaces. Water temperatures between about 125° C. and 130° C. showed comparatively better cleaning results than those at lower temperatures, but were still not sufficiently satisfactory. Hence, the subcritical deionized water should be at a temperature in a range between about 130° C. or 135° C. to about 220° C., including any variation or combination of ranges therein between. Typically, the water is used at a temperature between about 140° C. or 145° C. to about 215° C. or 218° C., or between about to about 148° C. or 152° C. to about 207° C. or 213° C. Desirable water temperatures may range between about 150° C. or 153° C. to about 210° C. or 212° C. about 154° C., 155° C., or 160° C. to about 202° C., 207° C., or 208° C., about 157° C., 165° C., 168° C., or 172° C. to about 190° C., 197° C., 200° C., or 205° C. Although designed to solve a problem experienced also in petrochemical reactions, the operating temperature range of between about 140° C. and 225° C. employed to regenerate catalyst activity in the present inventive process are much lower and distinct from those temperatures used in conventional catalyst regeneration methods. The use of a lower operating temperature and water is cost efficient in terms of both energy and renewable resources.

Depending on the nature or material used as catalyst in each of the vessels, the method can further include introducing a hydrogen peroxide solution to wash the catalyst surface and interior of the reactor. This wash may last for a period of between 6-18 hours, for example. This peroxide solution may be applied either at ambient room temperature or at an elevated, subcritical temperature. The hydrogen peroxide solution can be a deionized aqueous solution containing a concentration of between about 0.01% and about less than or equal to ≤7%, typically between about 4% to about 5% or about 6%, by volume of $H_2O_2$. According to an embodiment, the aqueous solution containing $H_2O_2$ can be applied to the first catalyst in the first vessel of the reactor for a period of up to 18 hours when catalytic activity of the first catalyst decreases to a predetermined level (e.g., ≤40% or 50% of original activity).

Additionally, one can introduce periodically an aqueous salt solution to either first or second catalysts in the reactor system, after reacting and removing the sugar solution feedstock and before introducing the subcritical deionized water rinse. In an embodiment, the aqueous salt solution is applied to the second catalyst in the second vessel of the reactor when catalytic activity of the second catalyst decreases to a predetermined level. The wash may last for a period of up to 16 hours, for example. One can then remove the aqueous $H_2O_2$ solution and the aqueous salt solution respectively from the first and second vessels of the reactor. Subsequently, the reactor and catalysts are rinsed with subcritical water of between about 140° C.-250° C. for a period of between 4-48 hours, for example.

Depending on the particular materials and poisons that have agglomerated to deactivate the catalyst, the subcritical water rinse can be applied to the catalyst for a period of between about 4 or 5 hours to about 24 or 48 hours or any duration therein between. Typically, the residence time of the subcritical water is for a period of between about 6 or 8 hours to about 25 or 30 hours; more typically, between about 7, 10, or 12 hours to about 18, 20, or 25 hours. Desirable rinse dwell times are between about 12 or 14 hours to about 16 or 22 hours.

The metal of the first catalyst can be a sponge-matrix metal catalyst or supported metal catalyst, such as Ni, and of the second catalyst can be either: Ru, Pt, or Pd, supported on a substrate, such as carbon or titania. As person familiar with catalysis mechanics, the morphological structure of supporting materials for catalysts can influence the chemical character and efficiency of the catalyzed reaction. Hence, what may apply to one species of catalyst and support may not be generalized easily to apply to similar catalyst systems. For instance, a system that uses a carbon-supported ruthenium (Ru/C) catalyst functions differently than a titania-supported ruthenium (Ru/$TiO_2$) catalyst. An appreciation of what may function in one system may not for the other is not conveyed.

The peroxide wash can be up to about 5% concentration, in a range between about 0.5% to about 5%. Typically, the peroxide wash is at a concentration between about 1% or 1.5% to about 4.5% or 4.8%; or, more typically between about 2% or 3% to about 3.5% or 4%.

The salt solution has a concentration a range between about 1% to about 10% concentrations. Typically, the salt concentration is between about 1% or 2% to about 7% or 8%. Preferably, the concentration is between about 3% to about 5% or 6%. The salt solution can be prepared from a variety of salt species, but typically the salts are either monovalent or dibasic salts (e.g., NaCl, KCl, $Na_2HPO_4$, $K_2HPO_4$, $Na_2SO_4$).

According to an embodiment, the catalyst is totally submerged within and allowed to soak in the wash solution, while minor agitation can be applied in the chamber. Agitation can be applied by either physical motion or gas bubbling through. Alternatively, one may apply a continuous flowing stream of washing solution to rinse over the catalyst surface.

In an alternative embodiment, the catalyst regeneration process may proceed as follows: after draining the reactor chamber of hydrogenation product, flushing the chamber with ambient temperature water, and then washing with a concentrated salt solution (e.g., NaCl or $K_2HPO_4$) at a temperature between 60° C. to 105° C. and over a period of 6-22 hrs. In other iterations, the salt solution wash is conducted at a temperature between about 60° C. and 85° C. for a period of about 8 hours to about 20 hours. Desirably, the substrate is washed with the salt solution at about 70° C. for about 12 hours. The catalyst is then washed with water for another 6 to 12 hours under the same temperature condition. Subsequently, the treated catalyst is washed with subcritical water at 170-250° C. for about 6-16 hours.

While the salt solution can be used with, for example, either a supported nickel or ruthenium catalyst or both systems, one can also introduce an additional peroxide solution wash, which is used with the nickel catalyst system alone.

After applying a hot water wash and either salt solution or peroxide wash, depending on catalyst material, the degree of polymerization (DP) can be reduced, for instance, by about 80% to about 85% relative to a used catalyst that is not treated according to the present regenerative method. The inventive process results in a more uniform distribution of the regenerated catalyst activity. It is believed that when exposing a sponge nickel or Ru/C catalyst, for example, to a salt solution for an extended time period, the solution helps removes impurities from protein absorbance, and remaining sulfur impurities are oxidized to either sulfate or sulfite, which can then be washed away by the subcritical water.

Treatment with hot water washing removes reactive organic compounds that may agglomerate to the catalyst and reactor surfaces. The catalyst exhibits regenerated catalytic activity after washing with the subcritical deionized water rinse, and a prolonged catalytic active duration of at least two to three (2×-3×) times longer than that of a catalyst that is not washed with the deionized subcritical water rinse.

Depending on catalyst performance and its retardation from sulfur poisoning, one can wash the catalysts in the reactor vessels with subcritical hot water as frequently as practicable and necessary. If significant retardation of the catalytic activity persists, one can wash with the catalyst in situ with a $H_2O_2$ solution or a salt solution, or in any order or combination of the three—peroxide, salt solution, and subcritical water. Of these three fluids, deionized subcritical hot water is employed most frequently. Usually, the number of times the salt solution rinse applied will be greater or more numerous than the number of times the peroxide solution is used. One can wash the first vessel catalyst with peroxide solution between about 1 to 3 or 4 applications for every 1 to 7 or 8 application of aqueous salt solution is applied to the first catalyst in the first vessel and the second catalyst in the second vessel. For example, the peroxide solution is used with sponge-nickel catalyst, but not with Ru/C catalyst, which is washed with the salt solution. Depending on the need for regeneration and type of agglomerated organics on the two different catalyst materials, the frequency of each kind of wash can be expressed as a ratio of peroxide to salt rinses (e.g., 1:1, 1:1.5, 1:2, 1:3, 1:4, 1:4.5, 1:5, 1:6, 1:7, or 1:8).

An advantage of the present method is that it permits regeneration of catalysts under relatively mild conditions by means of a simple process of washing with subcritical water and a salt solution rinse. The process removes chemi-absorption sulfur compounds from the catalyst surface, which can prolong the active life of the catalyst. This feature can lead to saving in both money and time for the manufacturer that hydrolyze sugars and other biologically-derived polysaccharides. The catalyst is restored to about 75% or greater of an initial catalytic activity level.

An unexpected result of the present invention is the relative efficiency that subcritical hot water has demonstrated in catalyst regeneration. Normally, water at ambient temperature is a poor solvent for sulfur compounds or organic oligomers, while supercritical water (temperature >374° C., pressure >221 atm) is extremely corrosive. One of the attractive features of hot-compressed water is the adjustability of its properties by varying process temperature and pressure. Specific to its solvent properties, the dielectric constant of water can be adjusted from 80 at room temperature (~20° C.) to 5 at its critical point. Therefore, water can solubilize most nonpolar organic compounds including most hydrocarbons and aromatics starting at 200-250° C.

B

The method described generally above can be adapted for used n a continuous hydrogenation reactor system, which can reduce catalytic deactivation. Hence, in another embodiment, the present inventive method provides continuous hydrogenation process. The process comprises: providing a hydrogenation reactor system with an in-take port and an extraction port, each of which respectively is connected in-line to an in-bound channel and an out-bound channel; introducing a carbohydrate or sugar solution feedstock and hydrogen into a reactor having a catalyst therein; reacting the feedstock under pressure; removing a resulting aqueous reaction product mixture; and periodically introducing a subcritical deionized water rinse into the first reactor when catalytic activity of the catalyst decreases to a predetermined level. The reactor and catalyst are rinsed with subcritical deionized water at a temperature, for example, between about 135° C.-220° C. for a period of between 4 to 24 or 48 hours. The reactor system is configured as with a first reactor section and second reactor section, each involving a different kind of catalyst material, such that a first part reaction involves a first catalyst material and a second part reaction involves a second catalyst material. The first and second reactor sections are arranged in series relative to each other. Each of the first and second reactors has a first reactor chamber and at least a parallel second reactor chamber. The first reactor chamber is used alternatively with the parallel second reactor chamber, such that a reactor chamber is washable with the subcritical deionized water rinse at a given time, without interruption of the hydrogenation process.

The continuous hydrogenation process may further include: introducing a deionized aqueous solution containing $H_2O_2$ in a concentration of ≤6% or 7% by volume to the first catalyst in the first reactor when catalytic activity of the first catalyst decreases to a predetermined level. Additionally, the process may involve introducing periodically an aqueous salt solution to either first or second catalyst in the reactor system, after reacting and removing the sugar solution feedstock and before introducing a subcritical deionized water rinse.

The first part of the washing using $H_2O_2$ is to remove sulfur and/or sulfides from front the catalyst. The aqueous salt solution is to remove agglomerated proteins from the catalyst. The catalyst exhibits regenerated catalytic activity after washing with the subcritical deionized water rinse. The catalyst exhibits a prolonged catalytic active duration of at least 2-3 times longer than that of a catalyst that is not washed with subcritical deionized water rinse.

The operational temperatures of the hot water washing typically can range between about 130° C. to about 250° C. Typically, the operations are conducted at a temperature between about 135° C. or 140° C. to about 220° C. or 225° C. More typically, the temperature range is between about 145° C. or 147° C. to about 212° C. or 215° C. In particular embodiments the temperature is between about 150° C. or 152° C. to about 205° C. or 208° C.

Figure 2:
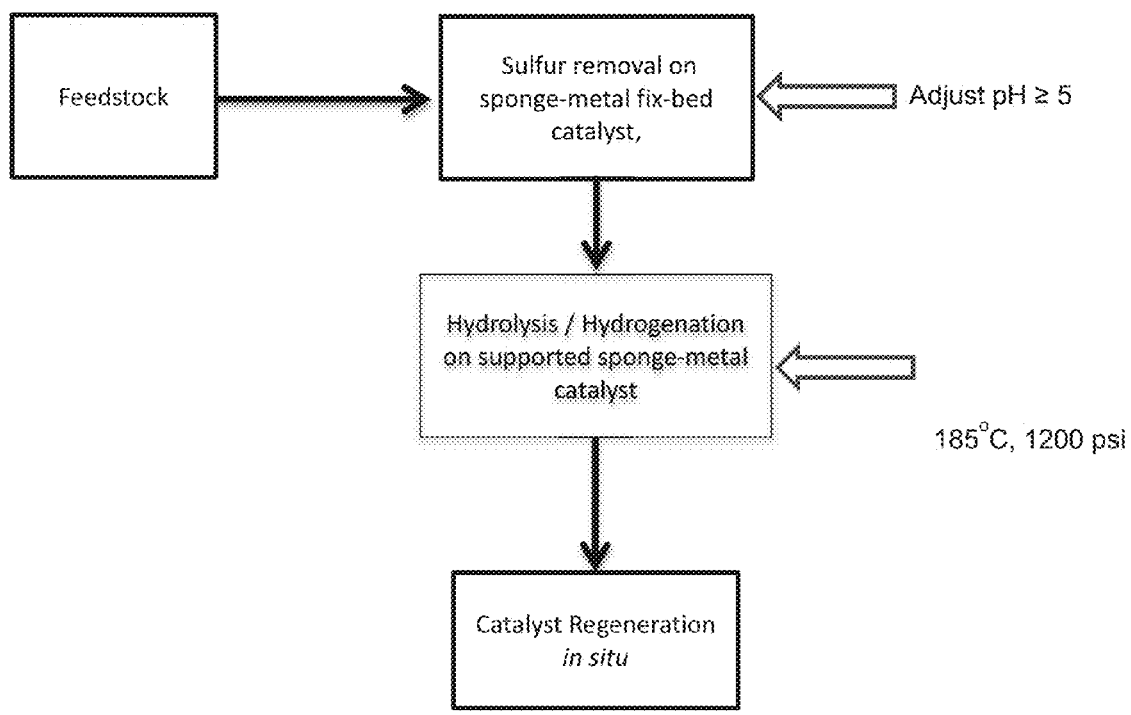
FIG. 2 is a flow chart showing a schematic representation of a process for hydrothermal liquefaction of biomass and hydrogenation/hydrolysis of sugars, and then regenerating the catalysts in situ according to an embodiment of the present inventive process.

FIG. 2 depicts a schematic representation of a hydrogenation process according to an embodiment of the present invention. This flow chart shows a feed stock of carbohydrate or sugar alcohols is introduced into a reactor having a first catalyst (e.g., Raney Ni) on a fixed-bed and reacted at an atmosphere of about 1100-1300 psi (e.g., 1200 psi), at a temperature less than or equal to about 140° C. or 150° C. (e.g., 130° C.), to remove sulfur and other containments. The feed is then discharged to a second reactor chamber here the material is subject to hydrogenation over a second kind of catalyst (e.g., Ru/C). Either one or both of the first and second catalysts can be a sponge-metal matrix catalyst. After a time, when the catalysts start to deactivate and catalytic activity flags, one regenerates the catalysts in situ according an embodiment of the present process.

Unlike in conventional sugar hydrogenation processes, in which sodium salts, sulfur and leach nickel need to be removed by means of an ion exchange process, an advantageous feature of the present invention is that we can eliminate the necessity for an ion exchange step in the present inventive process. According to an aspect of the present invention, we describe a continuous hydrogenation system and process that can enable catalyst regeneration in situ by means of a hot water wash. In other words, the regeneration does not require removing the catalysts from the reactor. Previously, the most common process of in situ regeneration was to oxygenate, or burn-off, the temporary poisons to resume catalytic activity.

As in typical hydrogenation processes, a feedstock of sugars is introduced and reacted with hydrogen in each of the first set of reactor chambers. However, the present invention involves a two-stage processing protocol. The first stage takes crude sugar solutions and reacts in the presence of a sacrificial sponge-metal (e.g., nickel) catalyst. The sponge-metal catalyst helps either to reduce the level of or remove sulfur contaminant in the feedstock. When a fresh catalyst has been used to an extent that its catalytic activity starts to flag, as detectable from the efficiency and purity of the reaction products, such that the activity of the catalyst decreases to a predetermined level (e.g., ≤50%, ≤60%, ≤70%, or ≤75% of initial activity) at which point regeneration is needed, one can shut off the feedstock directed to the chamber in which one desires to regenerate the catalyst.

According to feature of the present invention, the process involves a hydrogenation reactor system with an in-take port and an extraction port, each of which respectively is connected in-line to an in-bound channel and an out-bound channel, introducing a carbohydrate or sugar solution feedstock and hydrogen into a reactor having a catalyst therein, reacting the feedstock under pressure, removing a resulting aqueous reaction product mixture, and periodically introducing a subcritical deionized water rinse into said first reactor when catalytic activity of said catalyst decreases to a predetermined level. The reactor and catalyst are rinsed with subcritical deionized water at a temperature between about 135° C.-220° C. for a period of between 4-24 hours.

Figure 3:
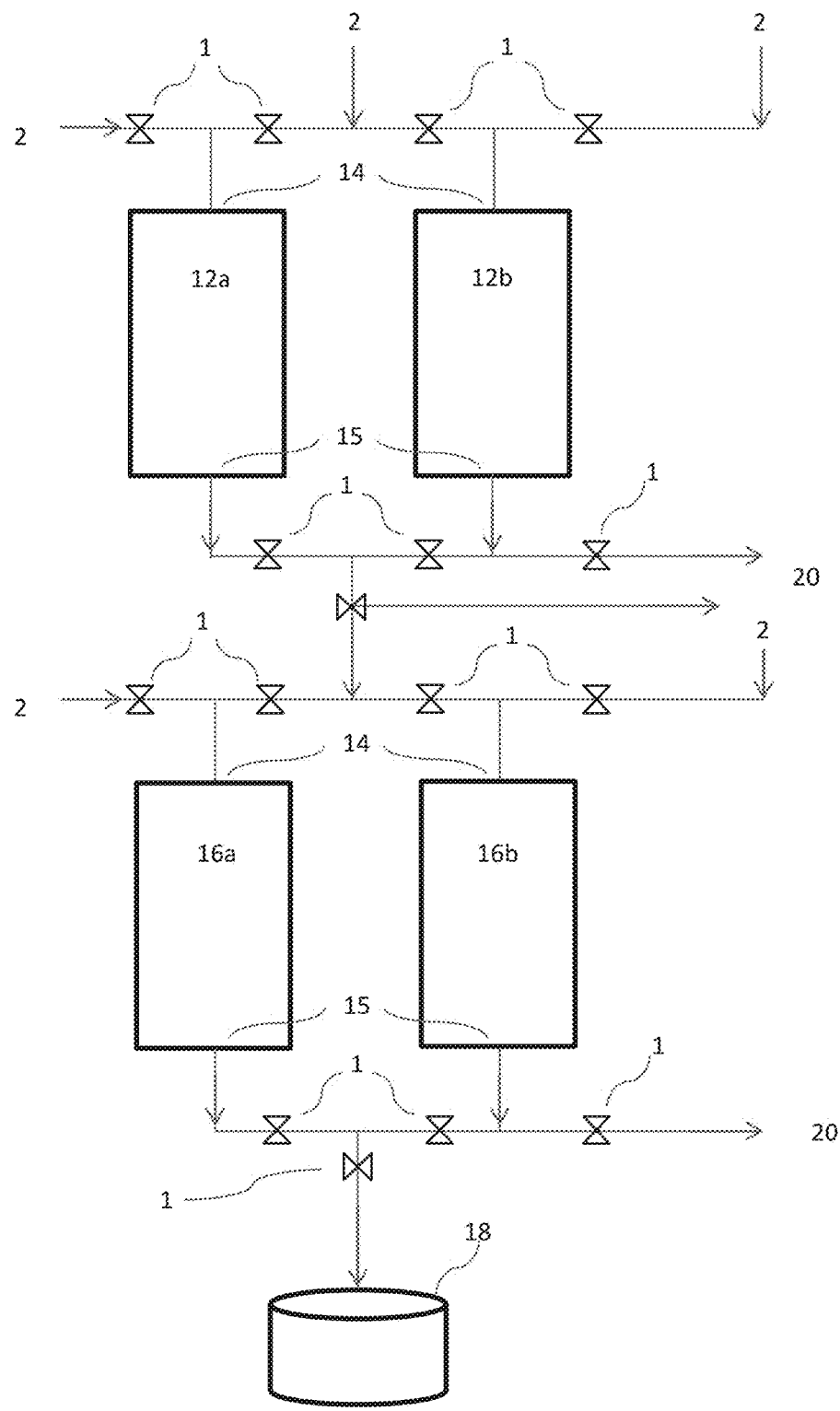
FIG. 3 is a schematic representation of an embodiment of a hydrogenation/hydrolysis system according an embodiment of to the present invention, in which parallel sets of reactors are used in series.

FIG. 3, shows a schematic representation of a reactor system 10 according to the present invention. The system has a first set of reaction chambers or vessels 12a, 12b arranged in parallel. The reaction chambers each have an inlet port 14 and an extraction or exit port 15. A feedstock source and reagents 2 are introduced, into each chamber through the inlet port 14 by means of connecting several tubes or channels. Reacted products, byproducts and waste 20 are removed from the chamber through the exit port 15.

The first set of reaction chambers can be connected to a second set of reaction chambers or vessels 16a, 16b that are also arranged in parallel. In each set of reactors there may be two chambers or more multiple chambers, depending on the size or scope of operations. The reactor are interconnected with conduit tubes or channels that are regulated with a number of valves 1, which can direct the flow of reagents and product to and from each set of reaction chambers. In other words, reaction product from each set of reactors can be channeled through the associated set of values and conduits/pipes. Depending of the operation, reaction products, as well as other fluids, from the first set of reactors 12a. 12b can be directed into either reactor chamber of the second set of reactors 16a, 16b or to other receptacles or waste 20. Hence the first reactor chamber is used alternatively with the parallel second reactor chamber, such that a reactor chamber is washable with the subcritical deionized water rinse at a given time, without interruption of the overall hydrogenation process in other reactor chambers. Desired reaction product can be collected in a container or other holding vessel 18. According to certain embodiments, a sponge-metal nickel catalyst (Ni) is situated within each of the first set of reaction chambers 12a, 12b. Likewise, in certain embodiments, a ruthenium on carbon (Ru/C) catalyst is used in each of the second set of reaction chambers 16a, 16b.

The reactor system is configured with a first reactor section and second reactor section, each a different kind of catalyst material (e.g., sponge nickel and Ru/C catalysts), such that a first part reaction involves a first catalyst material and a second part reaction involves a second catalyst material. As envisioned, the first part of the reactor assembly reacts to reduce or remove sulfur and/or sulfides from said feedstock, before reacting in a second part reaction. This we believe can help reduced poisoning the second catalyst in the second reactor, and help minimize adsorption of DP oligomers.

In the assembly, the first and second reactor sections are arranged in series relative to each other. Each of the first and second reactors has a first reactor chamber and at least a parallel second reactor chamber. The parallel configuration of the system permits one to take a chamber off-line without significantly impacting the continuous nature of the overall hydrogenation process in other chambers. Individual first and second vessels in each section can be arranged either in serial communication or alternatively, in parallel communication with each other that permits them to be connected to a continuous production line.

This combination of configurations is advantageous. Unlike conventional industrial batch-processing approaches in which the reactor chamber needs to be emptied and/or disassembled, the present invention enables continuous "online" regeneration of catalyst. Hence, the invention can improve the overall efficiency, production volume capacity, and reduce costs associated with hydrogenation of sugars or carbohydrates into polyhydric alcohols for various useful products. The hydrogenation catalyst occurs in-situ in the reactor. That is, in contrast to what is conventionally done, one does not need to remove the catalyst from the reactor chamber for regeneration.

According to the present invention, the spent catalyst can be regenerated either after introducing a spent catalyst from a reactor into a fixed bed regenerator, or in situ in the reactor chamber. That is, one can either unload the reactor for the washing, or preferably, the reactor can be washed in a continuous process. According to the latter, the catalyst can remain in the reactor chamber, which avoids the efforts associated with removing the catalyst and provides savings in both time and cost. The reactor system is well adopted for the present process, as an advantage of the present process is that one can regenerate the catalyst simultaneously with the sugar hydrogenation reaction. The regeneration process can be operated in the same temperature and pressure range as the hydrogenation reaction. Thus, one does not need to re-adjust conditions in a reactor vessel.

Section III—Empiricals

The examples in the present section further illustrate and describe the advantages and qualities of the present invention. The particular materials, dimensions, amounts and other parameters are exemplary, and are not intended to necessarily limit the scope of the invention. Hydrogenation of aqueous sugar solutions can be performed in batch and continuous reactors using supported nickel and ruthenium catalysts. In general the present invention can be applied to various "skeletal catalyst" or sponge-metal catalysts that have physical and chemical properties similar to those of Raney nickel. Preparation methods were precipitation, impregnation, sol-gel and template syntheses, and $SiO_2$, $TiO_2$, $Al_2O_3$ and carbon were used as support materials. In the particular examples discussed herein, we refer to Raney nickel catalysts and ruthenium on carbon catalysts (Ru/C). Generally, in the embodiments the reactor and catalyst are rinsed with subcritical deionized water at a temperature between about 130° C. or 135° C. to about 220° C. for a period of about 3 or 4 hours to about 24 hours.

A

Table 1 is a comparative summary showing the effect of various different regenerative treatments used to recover catalytic activity of a sponge-metal (i.e., Raney nickel) fixed-bed catalyst. A sugar feedstock with a dry solids (DS) content of about 30%, up to about 40%, is subjected to hydrogenation in the comparative examples. A wash with bleach for about 12 hours showed no regenerative effect at all. Heat treatment at 70° C. and no hydrogen for about 14 hours regenerates less than 10% of the catalyst activity. Washing the catalyst with hot water under about 1200 psi $H_2$ for about 4 hours at 200° C., regenerated about 80% activity. A 5% peroxide ($H_2O_2$) wash for about 24 hours appeared to have the best effect, restoring about 90-95% of catalytic activity.

TABLE 1

Comparison of Methods for Regeneration of Raney Ni-Catalyst

| Treatment | $H_2$ Pressure | Catalyst Activity Recovery (%) | Liquid Hourly Space Velocity (LHSV) | Time (hr.) |
|---|---|---|---|---|
| 70° C. wash | No | <10% | 1 | 14-24 hr |
| Bleach wash | No | 0% | 1 | 6-12 hr |
| 170° C. wash | 1200 psi | 80% | 1 | 4-10 hr |
| $H_2O_2$ wash | No | 90-95% | 1 | 6-24 hr |
| Feedtock: | 30% DS, 10% DP, 7 ppm of sulfur. | | | |
| Reaction condition: | Catalyst reduced under 1200 psi $H_2$, for 4-24 hrs, at 140° C. and 200° C., LHSV = 1 | | | |

As comparative examples, regeneration attempts that washed the catalyst bed with water and/or bleach at 70° C. for up to 24 hours were not effective. Catalyst activity exhibits no significant recovery or improvement as compared to before regeneration.

Figure 4:
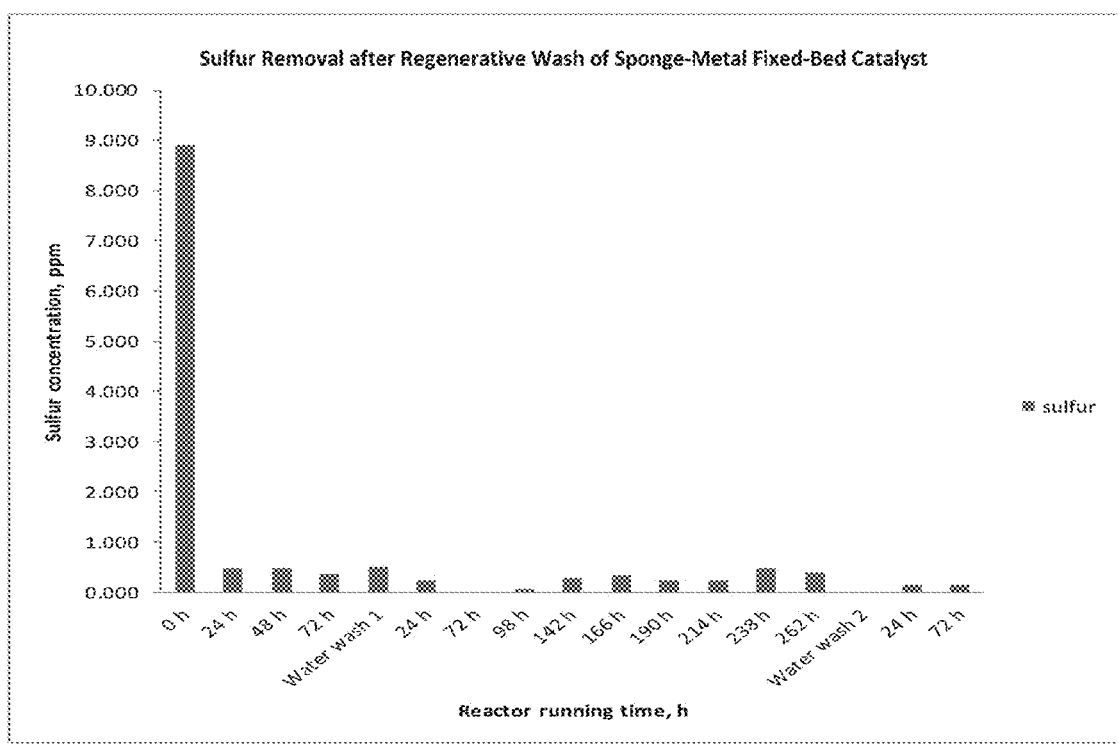
FIG. 4 is a graph showing efficiency of reducing the build-up of sulfur concentration on sponge-metal (e.g., Raney nickel) catalyst after regenerative washes according to the present invention.

FIG. 4 shows the relative concentration of sulfur (ppm) present on a sponge-metal (Ni) fixed-bed catalyst over time. At the beginning, the sulfur concentration is significant in the reactor (~8,800-8,900 ppm), but the nickel bed soon reduces the sulfur concentration to less than about 400 ppm or 500 ppm. This level is maintained after each regenerative treatment with hot water solution. These results suggest that sulfur poisoning can be effectively controlled and reduced.

Figure 5:
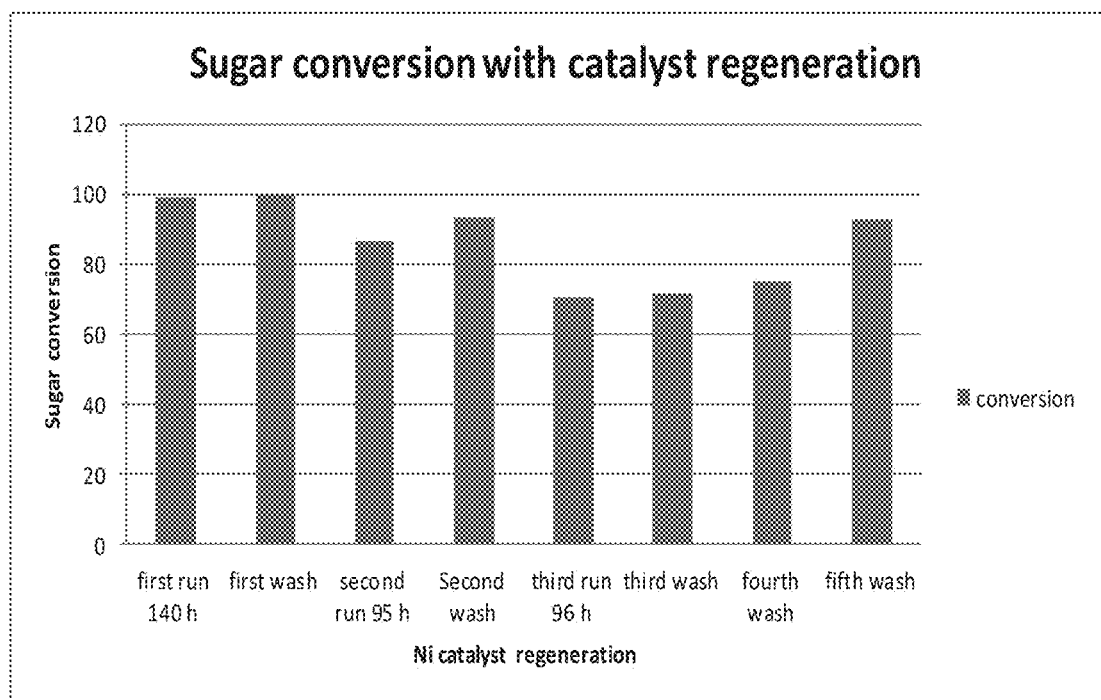
FIG. 5 is a graph showing relative efficiency of sponge-mental (e.g., Raney nickel) catalyst converting sugar after regenerative washes according to the present invention.

FIG. 5 presents the effect of regenerating a Raney nickel fixed-bed catalyst with subcritical hot water (170° C.), as expressed in terms of the relative percent efficiency of converting a sugar feedstock in hydrogenation reactions. Starting with a fresh catalyst, a first hydrogenation reaction runs for about 140 hours, after which the catalyst is washed. The first reaction run operated at near 100% efficiency converting sugar (i.e., ~97% or 98%). After the first wash with deionized subcritical water, the reaction exhibited similar or slightly better efficiency. A second reaction ran for about 95 hours, and exhibited a lower conversion rate (~85%-88%), which was increased to about 95% efficiency after a second regenerative wash. In a third reaction, run for about 96 hours, the efficiency rate had decreased to about 70%, which was increased slightly after a third regenerative wash; but increased to about 94% or 95% after a fourth and fifth washes. These results seem to suggest that the wash treatment temperature applied and/or duration of later washes may need to increase for later regenerative attempts.

Figure 6:
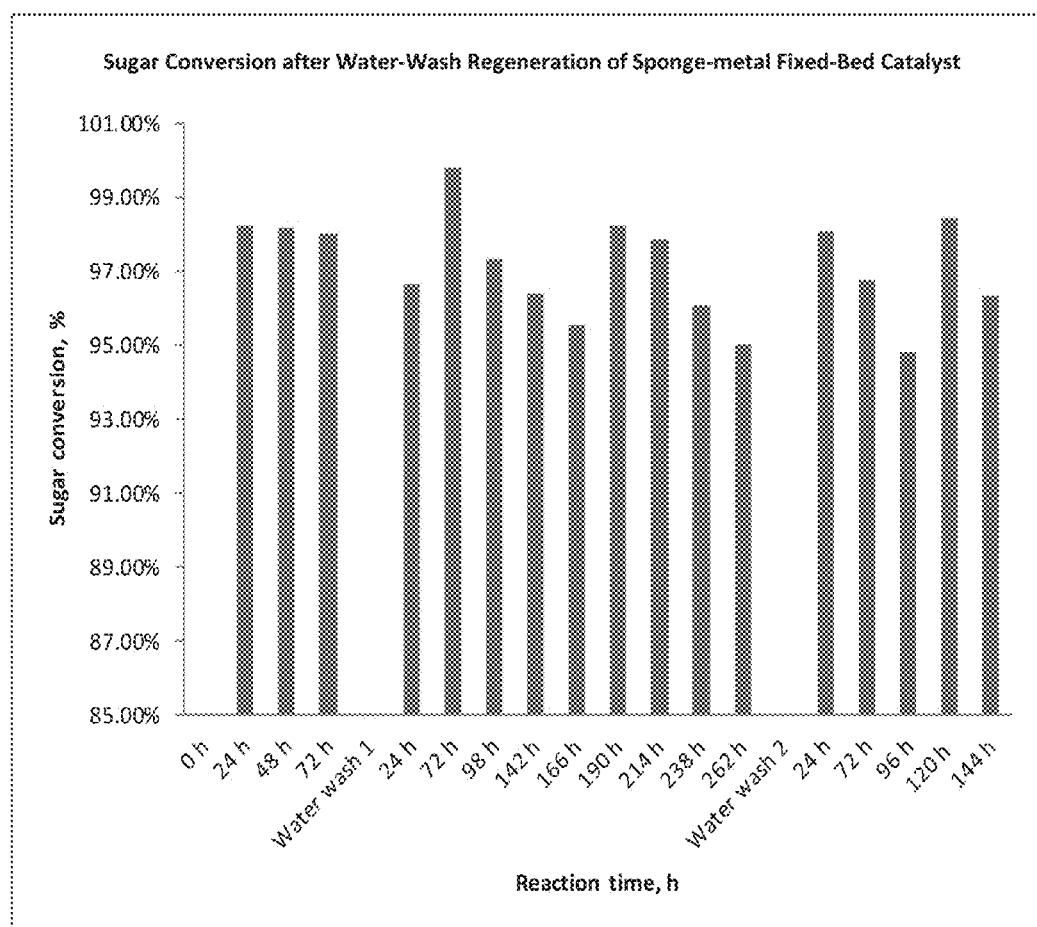
FIG. 6 is a graph showing relative efficiency of sugar conversation with sponge-metal (e.g., Raney nickel) catalyst after regenerative washes according to the present invention.

FIG. 6 summarizes relative efficiency of sugar conversation in a hydrogenation reaction over about an extended period during which sponge-metal catalysts were subjected to regenerative treatment with a hot water solution according to the present invention when the catalytic efficiency seemed to flag. As one can see, sugar conversion rates were maintained, at relatively high levels of about 94% or 95% or greater, like in FIG. 5. After each regenerative wash, sugar conversion increased from about 95% to about 98% with the same feed.

Figure 7:
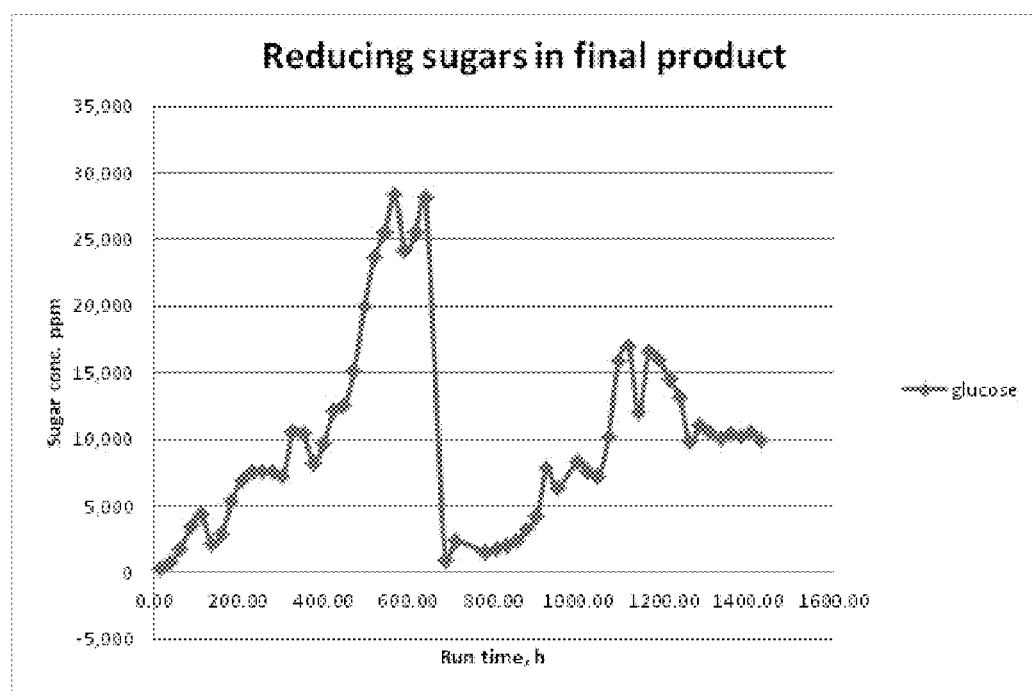
FIG. 7 is a graph showing a reduction in the concentration of sugar (ppm) remaining in a final product over an extended period of running a hydrogenation reaction after regenerative treatment according to an iteration of the present invention.

FIG. 7 shows that the amount of unreacted sugar that remains in a final product of the hydrogenation reaction can be significantly reduced. At the beginning of the hydrogenation reaction run, the amount of sugar concentration in the product is low, indicating that the catalyst is operating at high efficiency. Over the course of hydrogenation, the amount of unreacted sugar remaining in the product increases. At about 400 hours into the reaction run, the sugar concentration is at about 8,000-10,000 ppm; later at about 500 to 600 hours sugar levels have reach about 24,000-28,000 ppm, which for some commercial uses is unacceptable. Normally, when residual sugar levels reach sufficiently high concentrations, manufacturers will need to stop production and replace or modify the catalyst at this point. Stopping production and removing or regenerating the catalyst, however, tends to be costly and economically inefficient. Hence, the present in situ regenerative treatment and reactor system can help overcome such a problem, by providing a parallel reactor configuration that can make production continuous and eliminate the need to change catalysts after a relatively short production run.

After a regenerative treatment of the catalyst in the reactor, the graph in FIG. 7 shows that catalytic activity is restored, as evidenced by a return to relatively low sugar concentration remaining in product even after prolonged hydrogenation run times of about 700-900 hours. The catalyst is washed and rinsed with subcritical water and/or a salt solution (i.e., Ru/C) or a peroxide solution (i.e., Ni), according to a version of the present invention. The agglomerated species on the catalyst are removed. An interested phenomenon is that after the catalyst is subject to the regenerative wash, the concentration of sugar that remains in final product did not return to the initial high concentrations but remained at a moderate level.

B

All fixed-bed catalytic reactions described, in the following examples were performed 30 cubic centimeter (cc) fixed bed reactors. The reactor bodies are stainless steel with an internal diameter (ID) of 0.61 inches. The reactors are jacketed and are heated with circulating oil. Reactor temperatures are monitored via an internal thermowell ⅛" with a 1/16" thermocouple that can slide up and down to monitor peak temperature. The temperature of the jacket is monitored, by measuring the oil temperature just before it enters the jacket. The temperatures of the reactors are controlled by adjusting the oil temperature. The inlets of the reactors are attached to an Isco dual piston pump and mass flow controllers for supplying gases. The outlet was attached to a condenser kept at 5° C. by a chiller unit. The pressures of the reactors are controlled using a dome loaded back pressure regulator (Mity Mite brand).

In general the experimental conditions employed for the examples are:
Reactor jacket temperature: 140° C.-200° C.
Oil bath temperature: 90° C.
Reaction temperature; 80° C.
NaCl concentration: 40% by wt., total volume: 70 ml
Catalyst weight (wet): 20-25 g.
Sugar concentration: 30%-40% by wt.
Feed pH: 4.5-5.0
Hydrogen flow rate: 400 mL/min.
Pressure (H2) 1200 psi
Reaction time: 4 hrs.

EXAMPLE 1

Used Ru/C catalyst from a vertical trickle-bed reactor is subjected to regeneration. About 85% catalytic activity remained of the catalyst sample after about 16 hours of undergoing a hydrogenation reaction. Using about 70 mL of 40% NaCl solution was added to 25 grams of used Ru/C catalyst from both a top section and a bottom section of the reactor in 250 mL beaker, and the mixture was stirred for 4 hours at 70° C. The liquid was poured out and solid was added 100 ml DI water, and stirred for another 16 hours at 70° C. The solid catalyst was washed and rinsed with DI water five (5) times to removal, any extra residual salt. The oligomer deposits on the catalyst surface are nearly completely removed, and catalytic activity recovered to about 93% or 95% of previous level for fresh catalyst.

EXAMPLE 2

Similar to the conditions described in the example above, Ru/C catalyst was washed by hot water at 190° C. for 16 hours at 1200 psi, and then washed with 0.5% $H_3PO_4$ at 170° C. for 16 hours. This resulted in recovery of about 90%-95% of former catalytic activity.

EXAMPLE 3

In another regenerative example, after 240 hours of use in hydrogenation reaction, Ru/C catalyst is washed with hot water for 16 hours at 180° C. The catalyst activity was tested and found that the catalyst was able to convert 99% of the sugar feedstock to sugar alcohols.

EXAMPLE 4

Deactivated Ru/C catalysts (Sugar conversion, 85%) were loaded in a 30 cc reactor, DI water was introduced to reactor by HPLC pump at rate of 1 mL/min. The reactor was heated by outside oil jacket to 250° C. The catalyst was washed under high temperature for 16 hours, then cooled down to room temperature. Catalytic activity was restored to be near full recovery, ~98%.

EXAMPLE 5

Sponge nickel fixed-bed catalysts is employed for sulfur removal. A 30% dextrose solution was used as feed to check catalyst activity at LHSV=1, 140° C., 1200 psi $H_2$. After running hydrogenation reaction for 800-900 hours with, the catalyst activity dropped to about 70% and 75% sugar conversion, respectively and 95% sulfur absorbence (7 ppm to 1 ppm). After hydrogenation reaction, the catalyst was washed with subcritical water for 18 hours at 150° C. Catalytic activity is restored; sugar conversion recovered to about 94-96%.

EXAMPLE 6

Using a sponge-metal (Raney nickel) fixed-bed catalyst, carbohydrate hydrogenation reaction was run in a 30 cc reactor at a $H_2$ pressure of 1200 psi, at a reaction flow rate of 2 mL/min for more than 340 hours using different feedstocks (pH 5.5, 30% DS (8-10% DP)), which contained about 8 ppm to 12 ppm sulfur. The fix-bed was washed with subcritical hot water (170° C.) for about 4 hours to remove adsorbed sulfur compounds and regenerated the surfaces of the catalyst. After washing, the same feedstock was put into this reactor to test for relative efficiency of sugar conversion after the sulfur removal. The results are summarized in accompanying FIG. 5, discussed above.

The present invention has been described in general and in detail by way of examples. Persons of skill in the art understand that the invention is not limited necessarily to the embodiments specifically disclosed, but that modifications and variations may be made without departing from the scope of the invention as defined by the following claims or their equivalents, including other equivalent components presently known, or to be developed, which may be used within the scope of the present invention. Therefore, unless changes otherwise depart from the scope of the invention, the changes should be construed as being included herein.

I claim:

1. A method of regenerating hydrogenation catalyst activity in-situ, the method comprising: a) providing a hydrogenation reactor for carbohydrates, said reactor being configured to have at least a first and a second vessel, said first vessel having a first catalyst and said second vessel having a second catalyst, said first and second catalysts being either the same or of a different material, said first and second vessels are arranged either in serial communication or in parallel communication with each other; and b) rinsing each respective vessel and catalyst with subcritical deionized water of between about 130° C.-250° C. for an extended period.

2. The method according to claim 1, wherein said method further comprises: introducing a subcritical deionized aqueous solution containing $H_2O_2$ in a concentration of ≤7% by volume to said first catalyst in said first vessel of said reactor when catalytic activity of said first catalyst decreases to a predetermined level; or introducing periodically an aqueous salt solution to either 1) said first catalyst in first vessel or 2) said second catalyst when catalytic activity of said second catalyst decreases to a predetermined level; removing respectively said aqueous $H_2O_2$ solution from said first vessel and said aqueous salt solution from said first or second vessels of said reactor.

3. The method according to claim 1, wherein said first or second catalyst is a sponge matrix catalyst.

4. The method according to claim 3, wherein a metal of said first catalyst is Ni.

5. The method according to claim 3, wherein a metal of said second catalyst is selected from Ru, Pt, and Pd.

6. The method according to claim 2, wherein said aqueous $H_2O_2$ solution is applied to said first catalyst in first vessel once for each 1-8 applications of aqueous salt solution applied to said second catalyst in second vessel.

7. The method according to claim 1, wherein a degree of polymerization is reduced by at least 80%, relative to an untreated catalyst.

8. The method according to claim 1, wherein a degree of polymerization is reduced by at least 85%, relative to an untreated catalyst.

9. The method according to claim 2, wherein said catalytic activity of either said first catalyst or said second catalyst is restored to about 75% or greater of an initial catalytic activity level for each catalyst.

10. The method according to claim 1, wherein said predetermined level of catalytic activity of either said first catalyst or second catalyst is ≤75% of an initial catalytic activity level for each catalyst.

* * * * *